United States Patent [19]

Szilagyi et al.

[11] 4,329,457
[45] May 11, 1982

[54] PROCESS FOR THE PREPARATION OF 6-(SUBSTITUTED AMINO)-3-PYRIDAZINYLHYDRAZINES AND THEIR SALTS

[75] Inventors: Geza Szilagyi, Budapest; Peter Matyus, Esztorgom; Endre Kasztreiner, Budapest; Tibor Balogh, Budapest; Lajos Ila, Budapest, all of Hungary

[73] Assignee: Richter Gedeon Vegyészeti Gyár Rt., Budapest, Hungary

[21] Appl. No.: 147,224

[22] Filed: May 6, 1980

[30] Foreign Application Priority Data

May 7, 1979 [HU] Hungary ................. GO-1445

[51] Int. Cl.³ .............. C07D 413/02; C07D 237/20
[52] U.S. Cl. ............................ 544/114; 544/224; 544/238
[58] Field of Search .................. 544/224, 114, 238

[56] References Cited

U.S. PATENT DOCUMENTS 2,858,311 10/1958 Steck ................................. 544/224
3,717,632 2/1973 Anderson et al. ................. 544/224
3,769,278 10/1973 Pifferi et al. ..................... 544/224

Primary Examiner—Anton H. Sutto
Attorney, Agent, or Firm—Karl F. Ross

[57] ABSTRACT

The invention relates to a novel process for the preparation of 6-(substituted amino)-3-pyridazinylhydrazines having the general formula I

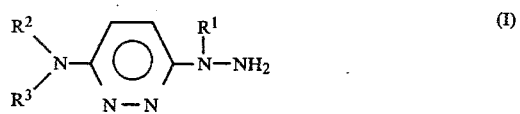

and their pharmaceutically acceptable acid addition salts, wherein $R^1$ stands for hydrogen atom or an alkyl group containing from 1 to 4 carbon atoms;

$R^2$ and $R^3$ may be the same or different and stand for alkyl groups containing from 1 to 6 carbon atoms, alkenyl groups containing from 2 to 6 carbon atoms, hydroxyalkyl groups containing from 2 to 4 carbon atoms, cycloalkyl groups containing from 3 to 8 carbon atoms, phenyl or benzyl groups or phenyl, benzyl or phenylethyl groups containing one or two halogen atoms, nitro, methoxy or hydroxyl groups, and one of $R^2$ and $R^3$ may stand also for a hydrogen atom, or $R^2$ and $R^3$ together with the neighboring nitrogen atom may build up also a morpholino, pyrrolidino, piperidino, heptamethyleneimino or N-methylpiperazino group.

The process consists in that a compound having the general formula II

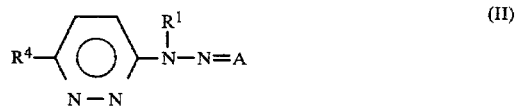

wherein $R^1$ is as defined above, $R^4$ stands for a chlorine or bromine atom or methylthio group, while A stands for a 1,7,7-trimethyl-2-bicyclo(2,2,1)heptylidene or a benzylidene group substituted by an $R^5$ group, wherein $R^5$ stands for hydrogen, chlorine or bromine atom, or a methoxy, nitro or methylsulphonyl group - is reacted with an amine having the general formula III

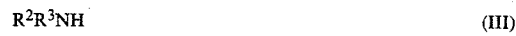

wherein $R^2$ and $R^3$ are as defined above - and the compound thus obtained having the general formula IV

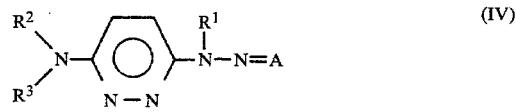

wherein $R^1$, $R^2$, $R^3$ and A are as defined above - is subjected to acidic hydrolysis.

The 6-(substituted amino)-3-pyridazinylhydrazines having the general formula I and prepared by the novel process of invention, possess a significant hypotensive effect as well as they are used as starting materials for the preparation of 6-(substituted amino)-3-pyridazinylhydrazines having a very significant hypotensive action.

2 Claims, No Drawings

PROCESS FOR THE PREPARATION OF 6-(SUBSTITUTED AMINO)-3-PYRIDAZINYLHYDRAZINES AND THEIR SALTS

This invention relates to a process for the preparation of 6-(substituted amino)-3-pyridazinylhydrazines having the general formula I (Il Farmaco Ed. Sci. 24, 919 (1966); J.Med. Chem. 18, 741 (1975)

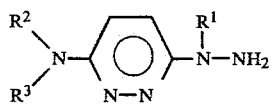

wherein
$R^1$ is hydrogen atom or an alkyl group containing 1 to 4 carbon atoms;
$R^2$ and $R^3$ may be the same or different and stand for alkyl groups containing 1 to 6 carbon atoms, alkenyl groups containing 2 to 6 carbon atoms, hydroxyalkyl groups containing 2 to 4 carbon atoms, cycloalkyl groups containing 3 to 8 carbon atoms, phenyl or benzyl groups or phenyl, benzyl or phenylethyl groups containing one or two halogen atoms, nitro, methoxy or hydroxyl groups, and wherein one of $R^2$ and $R^3$ can be hydrogen, or $R^2$ and $R^3$ together with the neighboring nitrogen atom can form a morpholino, pyrrolidino, piperidino, heptamethyleneimino or N-methyl-piperazino group,
as well as of their therapeutically acceptable acid addition salts.

These compounds possess a hypotensive effect and can be used as starting materials for the preparation of 6-(substituted amino)-3-pyridazinylhydrazones having very significant hypotensive action (Belgian Pat. No. 868,027).

Several processes have been described in the literature for the preparation of compounds having the formula I or of their salts. The principle of these consists in that the pyridazine ring is substituted firstly with the substituted amine and then with the hydrazine group.

According to the German Pat. No. 1,595,910 and U.S. Pat. No. 3,706,744 the compounds of formula I can be prepared by the reaction of a 3-chloro-6-(substituted amino)-pyridazine with an excess of 98% hydrazine hydrate. The yields of these reactions vary from 65 to 75%. The greatest disadvantage of this method is that the final product being formed as base during the process is unstable (this is noted in the patent description, too) and decomposition occurs under the given experimental conditions. Thus, it is complicated to obtain the compounds of formula I in a pure state. In addition, according to our own experiments, the yields mentioned cannot be reproduced, even when calculated for contaminated final products. These drawbacks obviously become more important when the process has to be realized in large-scale operations.

According to Belgian Pat. No. 772,365, 3,6-dichloropyridazine is reacted with substituted amines to yield 3-chloro-6-(substituted amino)-pyridazines in yields ranging from 40 to 70% and then these latter substances are brought into reaction with an excess of 98% hydrazine hydrate as is described in German Pat. No. 1,595,910 mentioned above. The inconveniences of this latter step have been emphasized above. The so-obtained impure compounds of formula I are purified in two steps, by forming 3-benzylidenehydrazino-6-(substituted amino)-pyridazine with benzaldehyde, recrystallizing the same and hydrolyzing it to the final product. However, the effectivity of this method cannot be judged because no yields are indicated in the cited Belgian Patent. Information concerning yields is found in a paper with the same substance as the Belgian Patent, published by the same authors (J. Med. Chem. 18, 741; 1975), according to which the average yield of the first step is 60.3%, that of the second step is 25.5%, while after the acidic hydrolysis (i.e. after the third and fourth steps) the average yield of the obtained final products amounts to 67.3%. Thus the average yield of compounds of formula I is 10.4%, i.e. very low, when calculated for the starting material. A further disadvantage lies in the experimental conditions for the acidic hydrolysis, i.e. the high temperature and long time of reaction, the partial efficacy of the hydrolysis and the loss in benzaldehyde which is very sensitive to oxidation.

According to Belgian Patent No. 821,389, 3-methylthio-6-chloropyridazine is reacted with the appropriate substituted amine and the obtained 3-methylthio-6-(substituted amino)-pyridazine is brought into reaction with an excess of hydrazine hydrate (the concentration of which is not specified) by refluxing in dimethylformamide for 40 hours, whereafter the crude final product is purified through the benzylidene derivative. The disadvantages are the same as above. A further drawback is the use of dimethyl formamide which reacts both with pyridazinylhydrazines or pyridazinylhydrazones at temperatures above 100° C., resulting in the formation of s-triazo-10(4,3-b)(pyridazine derivatives with splitting off of dimethyl amine and water [see, e.g. Croat. Chim. Acta 38, 299 (1966); Chem. Abstr. 66, 55, 458y (1967); Synthesis 1977, 176]. Thus the yields, which cannot be considered as suitable by any means, are further diminished by the side reactions.

The disadvantages of the above-mentioned and approximately analogous processes can be summarized as follows:

(a) The compounds having the formula I are formed under basic conditions and at high temperatures favoring the decomposition.

(b) The base obtained is highly contaminated; thus, it must be subjected to a purifying process consisting of two steps; the overall yields are, however, rather low after splitting off the protecting group by acidic hydrolysis at higher temperatures under the given experimental conditions.

(c) The use of dimethyl formamide can induce the formation of side products by which the yield is diminished.

(d) All steps of the reaction series should be carried out for the synthesis of each of the final products.

(e) Benzaldehyde, which is formed in course of hydrolysis of the protecting group, is recovered only with significant losses.

(f) The use of 98% hydrazine hydrate raises several problems concerning corrosion, safety of operation and hygiene (Hommel, G.: Handbuch der gefährlichen Güter, 272. Merkblatt, Springer Verlag, Berlin, 1970/73).

The aim of the present invention is to provide a process which, by eliminating the disadvantages of known processes, enables preparation of the compounds having the formula I in a simple way and on industrial scales.

The invention is based on the following recognitions:

(a) The reactivity of chlorine atom in 3-chloro-6-(substituted amino)-pyridazines is strongly diminished (R. N. Castle: Pyridazines, p. 248, ed. John Wiley and Sons, New York, 1973); thus, the substitution by hydrazine proceeds only with low to fair yields and in some cases no substitution occurs. It has been recognized, however, that by changing the color of introduction of substituents, on the one hand, and by preparing firstly a 3-(protected hydrazino)-6-chloro-pyridazine, on the other hand, the chlorine atom of compounds thus obtained is much more reactive and can be brought into nucleophilic substitution reactions with substituted amines in a simple way and in high yields.

(b) The protecting group of 3-(protected hydrazino)-6-(substituted amino)-pyridazines can be cleaved under mild conditions; thus, the final products having the formula I can be obtained from these intermediates in high yields.

These recognitions are really surprising for a person skilled in the art, too. Namely, it is known that one of the chlorine atoms in 3,6-dichloropyridazine is much more reactive and can easily be brought into a nucleophilic substitution reaction, while the second chlorine atom can be reacted only under strong conditions and in some cases cannot be reacted at all. Furthermore, it is an experimental fact that the chlorine atom of 3-chloro-6-pyridazinylhydrazine cannot be substituted by amines, or it is substituted with great difficulties and the reaction results in several decomposition products, owing to the strong conditions required. In addition, it is well-known that 3-benzylidenehydrazinopyridazines (and the related phthalazines) easily cyclize to the very stable s-triazolo(3,4-b)pyridazines (or to related triazolophthalazines, respectively) by heating [Tetrahedron 22, 2073 (1966); Helv. Chim. Acta 34, 195 (1951)]. Thus, it could not be expected that the chlorine atom of pyridazinylhydrazones can be replaced to give 6-(substituted amino)-3-pyridazinylhydrazones in high yield, without side reactions.

This recognition is surprising for a further reason, too. Namely, it was unexpected that final products having the formula I will be obtained in excellent yield and under mild conditions from these substituted pyridazinylhydrazones, after cleavage of the protecting group. On the contrary, on the basis of literature data [Liebigs Annalen 656, 119 (1962)] these hydrazones were expected to be stable or, at least, to be hydrolyzed only under vigorous conditions.

On the basis of the facts mentioned above, the invention is a process for preparing 6-(substituted amino)-3-pyridazinylhydrazines having the formula I

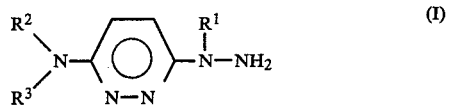

wherein
$R^1$ is hydrogen or an alkyl group of 1 to 4 carbon atoms;
$R^2$ and $R^3$ are the same or different and can be hydrogen, an alkyl group of 1 to 6 carbon atoms, an alkenyl group of 2 to 6 carbon atoms, a hydroxyalkyl group of 2 to 4 carbon atoms, a cycloalkyl group of 3 to 8 carbon atoms, phenyl or benzyl or a phenyl, benzyl or phenylethyl group containing one or two halogen atoms, nitro, methoxy or wherein hydroxyl groups, or $R^2$ and $R^3$ together with the neighboring nitrogen atom form a morpholino, pyrrolidino, piperidino, heptamethyleneimino or N-methylpiperazino group, as well as their therapeutically acceptable acid addition salts, which comprises reacting a compound having the formula II

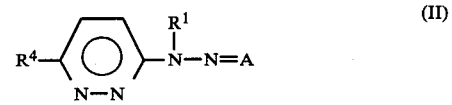

wherein $R^1$ is as defined above, $R^4$ stands for a chlorine or bromine or a methylthio group, and A is a 1,7,7-trimethyl-2-bicyclo(2,2,1)heptylidene or benzylidene group substituted by an $R^5$ group, wherein $R^5$ is hydrogen, chlorine or bromine, or a methoxy, nitro or methylsulphonyl group—with an amine having the formula III $$R^2R^3NH \qquad (III)$$

wherein $R^2$ and $R^3$ are as defined above—and subjecting the compound thus obtained having the formula IV

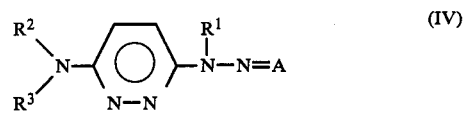

wherein $R^1$, $R^2$, $R^3$ and A are as defined above—to acidic hydrolysis.

The hydrazones having the formula II can be prepared by reacting 6-halo (or methylthio-)-3-pyridazinylhydrazines with the appropriately substituted benzaldehydes or camphor, respectively, by boiling in a solvent, in some cases by using an acid-type catalyst (e.g. acetic acid). The yields are very good. Short-chain alkanols are preferably used as solvents.

Of the compounds having the formula II, the benzylidene- as well as 4-nitro-, 4-chloro- and 4-methoxybenzylidenehydrazino derivatives are known in the literature [Tetrahedron 22, 2073 (1966); J. Pharm. Soc. Jap. 75, 778 (1955), i.e. Chem. Abstr. 50, 4970b (1956)], while 1,7,7-trimethyl-2-bicyclo 2,2,1)heptylidene-(6-chloro-3-pyridazinyl)-hydrazine can be obtained according to the process of Belgian Pat. No. 868,027.

In order to transform the compounds having the formula II into the compounds having the formula IV, the former compounds are reacted with the excess of an amine having the formula III (wherein $R^2$ and $R^3$ are as defined above), generally without any solvent or by using the excess of amine as solvent (which simultaneously plays the role of the acid binding agent), suitably at temperatures from 100° to 200° C. In some cases a polar additive, such as hexamethylphosporic acid triamide, is preferably used.

In order to transform the compounds having the formula IV into compounds having the formula I, it is suitable to carry out the reaction in a two-phase system consisting of a mixture of aromatic hydrocarbons, such as toluene or benzene, or halogenated hydrocarbons with aqueous solutions of mineral acids, such as hydrochloric, hydrobromic or sulphuric acid, at temperatures ranging from 20° to 60° C. The carbonyl component passes into the organic phase and can be recovered in a very good yield. The acid addition salts of compounds having the general formula I can be isolated from the phase containing the mineral acids in high yields, too.

The advantages of the process according to the invention, as compared to processes described in the literature, are as follows:

(a) The final product having the formula I can be obtained in two steps by starting from compounds having the formula II in a very favorable overall yield (as calculated for 6-chloro-3-pyridazinylhydrazine); the compounds of formula II can be obtained from the easily available 6-chloro-3-pyridazinylhydrazine with substituted benzaldehyde or camphor, respectively.

(b) Contrary to the processes known from the literature, the intermediates of the process according to the invention, i.e. compounds having the formulas II and IV, have high melting points and are easy to isolate, to purify and obtain with a favorable quality. The aimed product can be isolated in the pure form of its stable salt.

(c) A very advantageous feature of the process is that the carbonyl component, the acid and the organic solvents can be recovered and recirculated to the process with high yields.

(d) The single steps of the process can be carried out with high yields, in a simple and selective manner. Thus, these steps are suitable for use in continuous production on an industrial.

Further details of the invention are given in the following non-limiting Examples.

EXAMPLE 1

4-Nitrobenzylidene-(6-morpholino-3-pyridazinyl)-hydrazine

Step a:

4-Nitrobenzylidene-(6-chloro-3-pyridazinyl)-hydrazine

A mixture of 14.5 g (0.1 moles) of 6-chloro-3-pyridazinylhydrazine, 145 ml of ethanol and 15.1 g (0.1 moles) of 4-nitrobenzaldehyde is refluxed with stirring for 2 hours, cooled and 75 ml of water are added. The precipitate is filtered, washed with water, triturated with hot ethanol, filtered again and dried to give 25.4 g (91.5%) of the named compound; m.p. 290° C. (with decomposition).

The following compounds were prepared by the same process (Example 1, Step a):

3-nitrobenzylidene-(6-chloro-3-pyridazinyl)-hydrazine, m.p. 297°–300° C.;

4-methylsulphonyl-benzylidene-(6-chloro-3-pyridazinyl)-hydrazine, m.p. 282°–285° C.;

1-methyl-1-(6-chloro-3-pyridazinyl)-2-(4-nitrobenzylidene)-hydrazine, m.p. 272°–274° C.

Benzylidene-, 4-chlorobenzylidene- and 4-methoxybenzylidene-(6-chloro-3-pyridazinyl)-hydrazine are starting materials known from the literature [Tetrahedron 22, 2073 (1966)].

Step b:

4-Nitrobenzylidene-(6-morpholino-3-pyridazinyl)-hydrazine

The mixture of 5.55 g (20 mmoles) of 4-nitrobenzylidene-(6-chloro-3-pyridazinyl)-hydrazine [prepared by the process described in Step a:], 7.66 g (88 mmoles) of morpholine and 5.5 ml of hexamethylphosphoric cid triamide is heated at 150° C. for 24 hours. After cooling, the mixture is triturated with 56 ml of water, the precipitate is filtered, washed with cold ethanol and dried to give 5.6 g (85%) of the named compound; m.p. 245° C. (with decomposition).

The compounds, having the formula IV and obtained by the process described above, using the appropriately substituted benzylidene-(6-chloro-3-pyridazinyl)-hydrazine as starting material, are shown in Table I.

TABLE I

| Example No. | Name of the compound | M.P. °C. | Yield % |
|---|---|---|---|
| 2 | 3-Nitrobenzylidene-A | 255(d) | 63 |
| 3 | 4-Chlorobenzylidene-A | 263(d) | 71.5 |
| 4 | 4-Methoxybenzylidene-A | 246–249(d) | 80.5 |
| 5 | 4-Methylsulphonyl-benzylidene-A | 288–291 | 57 |
| 6 | Benzylidene-A | 259(d) | 78 |
| 7 | 1-Methyl-1-(6-morpholino-3-pyridazinyl)-2-(4-nitro-benzylidene)-hydrazine | 225–228 | 87.5 |

Notes to Table I:
A = (6-morpholino-3-pyridazinyl)-hydrazine
(d) = decomposition

EXAMPLE 8

1,7,7-Trimethyl-2-bicyclo(2,2,1)heptylidene-(6-morpholino-3-pyridazinyl)-hydrazine Step a:

1,7,7-Trimethyl-2-bicyclo(2,2,1)heptylidene-6-chloro-3-pyridazinyl)-hydrazine

A mixture of 15.2 g (0.1 moles) of camphor, 152 ml of ethanol, 15.2 g (0.105 moles) of 6-chloro-3-pyridazinylhydrazine and 15.2 ml of acetic acid is refluxed while stirring for 6 hours, then the solvent is removed under vacuum and the residue poured into 152 ml of water. The precipitate is filtered, washed with water several times and dried to give 30.7 g (90.5%) of acetate of the named compound; m.p. 134°–137° C. (after recrystallization from 85% aqueous ethanol).

Step b:

1,7,7-Trimethyl-2-bicyclo(2,2,1)heptylidene-(6-morpholino-3-pyridazinyl)-hydrazine A mixture of 33.9 g (0.1 moles) of 1,7,7-trimethyl-2-bicyclo(2,2,1)heptylidene-(6-chloro-3-pyridazinyl)-hydrazine acetate and 43.5 g /0.5 moles/ of morpholine is reacted while stirring at 145° C. for 8 hours. Then the excess of morpholine is removed under vacuum, the residue is triturated with 100 ml of water, filtered and dried to give 30.5 g (92.6%) of the title compound; m.p. 188°–190° C. (after recrystallization from ethanol).

Note: Steps a and b can also be contracted in such a way that in the course of working up of the reaction mixture of Step a, the solvents are removed under vacuum and the residue is brought into reaction with morpholine.

The compounds, having the formula IV and obtained by the process described in Example 8, Step b by using 1,7,7-trimethyl-2-bicyclo(2,2,1)heptylidene-(6-chloro-3-pyridazinyl)-hydrazine acetate [prepared by the process of Example 8, Step a], are shown in Table II.

TABLE II

| Example No. | Name of the compound | Reaction conditions °C./hours | M.P. °C. | Yield % |
|---|---|---|---|---|
| 9 | B-(6-Dimethylamino-3-pyrid- | | | |

TABLE II-continued

| Example No. | Name of the compound | Reaction conditions °C./hours | M.P. °C. | Yield % |
|---|---|---|---|---|
| | azinyl)-hydrazine | 150/24 | 176–179 | 76 |
| 10 | B-[6-bis(2-hydroxyethyl)-amino-3-pyridazinyl-hydrazine | 180/72 | 225–228 | 45 |
| 11 | B-[6-N-(2-hydroxy-1-propyl)-N-methylamino-3-pyridazinyl]-hydrazine | 150/20 | oil* | 82 |
| 12 | B-(6-Pyrrolidino-3-pyridazinyl)-hydrazine | 150/20 | 195–197 | 79.5 |
| 13 | B-(6-Piperidino-3-pyridazinyl)-hydrazine | 150/18 | 161–163 | 68.5 |
| 14 | B-(6-Heptamethyleneimino-3-pyridazinyl)-hydrazine | 160/36 | 164–156 | 75 |
| 15 | B-[6-(4-Methylpiperazino)-3-pyridazinyl]-hydrazine | 155/8 | 188–189** | 80.5 |
| 16 | B-(6-Cyclohexylamino-3-pyridazinyl)-hydrazine | 150/36 | 228–231 | 21.5 |

Notes to Table II:
B = 1,7,7-Trimethyl-2-bicyclo(2,2,1)heptylidene
*the $R_f$ value is 0.45 after developing on Silicagel HF$_{254}$ by a solvent mixture of benzene-methanol 85:15 and detecting by UV light or iodine vapors
** m.p. 201–204° C. according to Belgian Patent No. 868,027, i.e. crystal dimorphism exists.

EXAMPLE 17

6-Morpholino-3-pyridazinylhydrazine

Method A:

A mixture of 32.9 g (0.1 moles) of 1,7,7-trimethyl-2-bicyclo(2,2,1)heptylidene-(6-morpholino-3-pyridazinyl)-hydrazine (prepared by the process of Example 8, Step b), 660 ml of chloroform and 660 ml of concentrated hydrochloric acid is heated at 60° while stirring under a nitrogen atmosphere for 6 hours in such a way that the chloroform layer is separated from the reaction mixture every hour and replaced by fresh solvent (660 ml). The camphor recovered can be condensed with 6-chloro-3-pyridazinylhydrazine to give pure 1,7,7-trimethyl-2-bicyclo(2,2,1)heptylidene-(6-chloro-3-pyridazinyl)-hydrazine in 65–72% yield.

The aqueous phase is filtered, evaporated to dryness under vacuum and the residue is triturated thoroughly with a 1:1 mixture of ethanol and ether to give 24.95 g (92.4%) of dihydrochloride of the named compound; m.p. 233°–236° C.

The compounds having the formula I and obtained by the process described above (Example 17, Method A) are shown in Table III.

TABLE III

| Example No. | Name of the compound | M.P. °C. | Yield % |
|---|---|---|---|
| 18 | 6-Dimethylamino-3-pyridazinyl-hydrazine . 2HCl | 238–240 | 69.5 |
| 19 | 6-bis(2-Hydroxymethyl)-amino-3-pyridazinylhydrazine . 2HCl | 186–188(d) | 46.5 |
| 20 | 6-N-(2-Hydroxy-1-propyl)-N-methyl-amino-3-pyridazinyl-hydrazine . 2HCl | 185–186 | 54.5 |
| 21 | 6-Pyrrolidino-3-pyridazinyl-hydrazine . 2HCl | 233–235 | 76.5 |
| 22 | 6-Piperidino-3-pyridazinyl-hydrazine . 2HCl | 206–208(d) | 69 |
| 23 | 6-Heptamethyleneimino-3-pyridazinylhydrazine . 2HCl | 215–217 | 51.5 |
| 24 | 6-(4-Methylpiperazino)-3-pyridazinylhydrazine . 3HCl . 2H$_2$O | 228–231 | 92 |
| 25 | 6-Cyclohexylamino-3-pyridazinylhydrazine . 2HCl | 228–231 | 42 |

Note to Table III:
(d) = decomposition

Method B:

One part by weight of the substituted benzylidenehydrazine (compounds of Examples 1 to 6) is heated together with 20 parts by volume of benzene (or toluene or dichloromethane or chloroform) and 20 parts by volume of concentrated hydrochloric (or 48% hydrobromic) acid while stirring at an internal temperature of 40° C. for 1 to 2 hours in such a way that the organic phase is replaced by fresh solvent every 30 minutes. After separation 80–90% of the substituted benzaldehyde can be recovered from the organic phase. From the acidic aqueous phase, 6-morpholino-3-pyridazinylhydrazine dihydrochloride (or dihydrobromide, respectively) is obtained after evaporation and triturating the residue with ethanol and ether.

The reaction conditions and yields for 6-morpholino-3-pyridazinylhydrazine prepared as described above [Example 17, Method B] are shown in Table IV.

TABLE IV

| No. of the starting material (Example No.) | Conditions for reaction | Yield* % |
|---|---|---|
| 1 | toluene/conc . HCl | 88 |
| | CHCl$_3$/conc . HCl | 78.5 |
| | CH$_2$Cl$_2$/48% HBr | 72.5** |
| 2 | CH$_2$Cl$_2$/conc . HCl | 88 |
| 3 | CH$_2$Cl$_2$/conc . HCl | 81 |
| 4 | CH$_2$Cl$_2$/conc . HCl | 83 |
| 5 | toluene/conc . HCl | 34 |
| 6 | toluene/conc . HCl | 87 |

Notes to Table IV:
*dihydrochloride
**dihydrobromide

EXAMPLE 26

1-Methyl-1-(6-morpholino-3-pyridazinyl)-hydrazine 3.4 g (10 mmoles) of 1-methyl-1-(6-morpholino-3-pyridazinyl)-2-(4-nitrobenzylidene)-hydrazine [prepared by using the process of Example 1, Step b] are heated together with 68 ml of toluene and 68 ml of concentrated hydrochloric acid while stirring at an internal temperature of 40° C. for 90 minutes such that the organic phase is separated and replaced by fresh solvent every 30 minutes. After the reaction has been finished and the phases have been separated, the aqueous acid phase is evaporated to dryness under vacuum, the residue taken up in ether, the precipitate filtered and dried to give 2.2 g (78%) of dihydrochloride of the named compound; m.p. 171°–174° C.

What we claim is:

1. A process for the preparation of a compound having the formula I

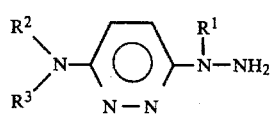

wherein
R¹ is hydrogen or an alkyl group of 1 to 4 carbon atoms;
R² and R³ are the same or different and are each alkyl groups of 1 to 6 carbon atoms, alkenyl groups of 2 to 6 carbon atoms, hydroxyalkyl groups of 2 to 4 carbon atoms, cycloalkyl groups of 3 to 8 carbon atoms, phenyl or benzyl, or phenyl, benzyl or phenylethyl groups containing one or two halogen atoms, nitro, methoxy or hydroxyl groups, and wherein one of R² and R³ can be hydrogen, or R² and R³ together with the neighboring nitrogen atom can form a morpholino, pyrrolidino, piperidino, heptamethyleneimino or N-methylpiperazino group,
or a therapeutically acceptable acid-addition salt of the compound, which comprises reacting a compound having the formula II

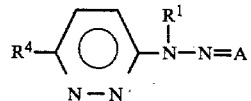

wherein R⁴ is chlorine or bromine or methylthio, and A is 1,7,7-trimethyl-2-bicyclo(2,2,1)heptylidene or a benzylidene substituted with an R⁵ group, wherein R⁵ is hydrogen, chlorine or bromine, or a methoxy, nitro or methylsulphonyl group—with an amine having the formula III $R^2R^3NH$     III at a temperature of 100° to 200° C. and subjecting the compound thus obtained having the formula IV

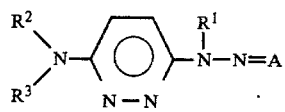

to acidic hydrolysis at 20° to 60° C. in a two-phase system comprising a hydrocarbon phase and an aqueous phase containing a mineral acid.

2. The process defined in claim 1 wherein the amine of the formula (III) is present in an amount in excess of the compound of formula (II).

* * * * *